(12) United States Patent
Leonard

(10) Patent No.: US 8,076,319 B2
(45) Date of Patent: *Dec. 13, 2011

(54) TREATMENT OF CONDITIONS RELATING TO HORMONE DEFICIENCIES BY ADMINISTRATION OF PROGESTINS

(75) Inventor: Thomas W. Leonard, Wilmington, NC (US)

(73) Assignee: Barr Laboratories, Inc., Woodcliffe Lake, NJ (US)

( * ) Notice: Subject to any disclaimer, the term of this patent is extended or adjusted under 35 U.S.C. 154(b) by 14 days.

This patent is subject to a terminal disclaimer.

(21) Appl. No.: 12/700,078

(22) Filed: Feb. 4, 2010

(65) Prior Publication Data
US 2010/0137265 A1 Jun. 3, 2010

Related U.S. Application Data

(60) Continuation of application No. 12/192,352, filed on Aug. 15, 2008, now Pat. No. 7,683,047, which is a division of application No. 10/678,828, filed on Oct. 3, 2003, now Pat. No. 7,427,609, which is a continuation of application No. 10/147,366, filed on May 16, 2002, now abandoned.

(60) Provisional application No. 60/291,488, filed on May 16, 2001.

(51) Int. Cl.
*A61K 31/56* (2006.01)
(52) U.S. Cl. ........................................ 514/171; 514/182
(58) Field of Classification Search .................. 514/171, 514/182
See application file for complete search history.

(56) References Cited

U.S. PATENT DOCUMENTS

| | | | |
|---|---|---|---|
| 4,425,339 A | 1/1984 | Pitchford | |
| 5,043,331 A | 8/1991 | Hirvonen et al. | |
| 5,108,995 A | 4/1992 | Casper | |
| 5,208,225 A | 5/1993 | Boissonneault et al. | |
| 5,827,843 A | 10/1998 | Koninckx | |
| 5,877,219 A * | 3/1999 | Willson | 514/617 |
| 5,891,867 A | 4/1999 | Lanquetin et al. | |
| RE36,247 E | 7/1999 | Plunkett et al. | |
| 5,935,949 A | 8/1999 | White | |
| 7,427,609 B2 * | 9/2008 | Leonard | 514/171 |

FOREIGN PATENT DOCUMENTS

| WO | WO 98/06404 | 2/1998 |
|---|---|---|
| WO | WO 00/74684 | 12/2000 |

OTHER PUBLICATIONS

Medline Abstract No. 97217050, Kumar, Indian Journal of Experimental Biology, (May 1996) 34(5), 391-402.
Medline Abstract No. 96432582, Oka et al., Japanese Journal of Pharmacology, (Jun. 1996) 71(2), 89-100.
Medline Abstract No. 97074593, Smith et al., CA: A Cancer Journal for Clinicians, (Nov.-Dec. 1996), 46(6), 343-63.
Simon et al., *Unscheduled Bleeding During Initiation of Continuous Combined Hormone Replacement Therapy: A Direct Comparison of Two Combinations of Norethindrone Acetate and Ethinyl Estradiol to Medroxyprogesterone Acetate and Conjugated Equine Estrogens*, Menopause, The Journal of the North American Menopause Society, vol. 8, No. 5. 2001. pp. 321-327.
Pickar et al., *Endometrial Effects of Lower Doses of Conjugated Equine Estrogens and Medroxyprogesterone Acetate*. Fertility and Sterility. vol. 76. No. 1. Jul. 2001, pp. 25-31.
Chesnut et al., *A Randomized Trial of Nasal Spray Salmon Calcitonin in Postmenopausal Women With Established Osteoporosis: The Prevent Recurrence of Osteoporotic Fractures Study*, The American Journal of Medicine, vol. 109. Sep. 2000. pp. 267-276.
Archer et al., *Effects of Lower Doses of Conjugated Equine Estrogens and Medroxyprogesterone Acetate on Endometrial Bleeding*. Fertility and Sterility. vol. 75, No. 6. Jun. 2001, pp. 1080-1087.
Dawson et al., *A Randomized Study Comparing Standard Versus Moderately High Dose Megestrol Acetate for Patients With Advanced Prostate Carcinoma Cancer* vol. 88, No. 4, Feb. 15, 2000, pp. 825-834.
Farinha et al., *Improved Bioavailability of a Micronized Megestrol Acetate Tablet Formulation in Humans*, Drug Development and Industrial Pharmacy, vol. 26, No. 5, 2000, pp. 567-570.
Naing et al., *Megestrol Acetate Therapy and Secondary Adrenal Suppression*, Cancer, vol. 86, No. 6, Sep. 15, 1999, pp. 1044-1049.
Bernhard et al., *Quality of Life in Postmenopausal Patients With Breast Cancer After Failure of Tamoxifen: Formestane Versus Megestrol Acetate as Second-Line Hormonal Treatment*, European Journal of Cancer. vol. 35, No. 6, 1999, pp. 913-920.
Loprinzi et al., *Randomized Comparison of Megestrol Acetate Versus Dexamethasone Versus Fluoxymesterone for the Treatment of Cancer Anorexia/Cachexia*, Journal of Clinical Oncology, vol. 17, No. 10, Oct. 1999, pp. 3299-3306.
Engelson et al., *Effects of Megestrol Acetate and Testosterone on Body Composition in Castrated Male Sprague-Dawley Rats*, Nutrition. vol. 15, No. 6, 1999, pp. 465-473.
Critchley et al., *Effects of Estrogen and Progesterone on the Endometrium*, Estrogens and Progestagens in Clinical Practice, edited by Fraser et al., 1998, pp. 145-161.
Ross et al., *Endometrial Effects of Three Doses of Trimegestone a New Orally Active Progestogen, On the Postmenopausal Endometrium*. Maturitas, vol. 28. 1997. pp. 83-88.
Conard et al., *Cardiovascular Risk Factors and Combined Estrogen-Progestin Replacement Therapy: A Placebo-Controlled Study With Nomegestrol Acetate and Estradiol*, Fertility and Sterility, vol. 64, No. 5, Nov. 1995, pp. 957-962.
Sturdee et al., *Is the Timing of Withdrawal Bleeding a Guide to Endometrial Safety During Sequential Oestrogen-Progestagen Replacement Therapy?*, The Lancet, vol. 334, Oct. 8, 1994, pp. 979-982.

(Continued)

*Primary Examiner* — Raymond Henley, III

(74) *Attorney, Agent, or Firm* — Myers Bigel Sibley & Sajovec, PA

(57) ABSTRACT

The present invention includes methods for preventing endometrial hyperplasia associated with estrogen therapy through the administration of a progestin agent. The methods presented may include starting the administration of a progestin agent at a high dose, and then lowering the dose.

9 Claims, No Drawings

OTHER PUBLICATIONS

Von Roenn, *Randomized Trials of Megestrol Acetate for AIDS-Associated Anorexia and Cachexia*, Oncology, vol. 51, Suppl 1. 1994, 19-24.

Espie, *Megestrol Acetate in Advanced Breast Carcinoma*, Oncology, vol. 51, Suppl 1, 1994, pp. 8-12.

Loprinzi et al., *Megestrol Acetate for the Prevention of Hot Flashes*, The New England Journal of Medicine, vol. 331. No. 6, Aug. 11, 1994, pp. 347-352.

Sporrong et al., *A Novel Statistical Approach to Analysis of Bleeding Patterns During Continuous Hormone Replacement Therapy*. Maturitas, vol. 11, 1989, pp. 209-215.

Schacter et al., *Megestrol Acetate: Clinical Experience*, Cancer Treatment Reviews, vol. 16, 1989, pp. 49-63.

Sporrong et al., *Comparison of Four Continuously Administered Progestogen Plus Oestradiol Combinations for Climacteric Complaints*, British Journal of Obstetrics and Gynaecology, vol. 95, Oct. 1988, pp. 1042-1048.

Alexieva-Figusch et al., *Treatment of Metastatic Breast Cancer Patients With Different Dosages of Megestrol Acetate; Dose Relations, Metabolic and Endocrine Effects*, Eur J Cancer Clin Oncol, 1984, pp. 33-40.

Canetta et al., *Megestrol Acetate*, Cancer Treatment Reviews, vol. 10, 1983, pp. 141-157.

Whitehead et al., *Actions of Progestins on the Morphology and Biochemistry of the Endometrium of Postmenopausal Women Receiving Low-Dose Estrogen Therapy*, Am. M. Obstet. Gynecol. vol. 142, No. 6, Mar. 15, 1982, pp. 791-795.

*Megestrol Acetate*, LARC Monographs on the Evaluation of the Carcinogenic Risk of Chemicals to Humans, vol. 21, 1979, pp. 431-439.

Donkervoort et al., *Megestrol Acetate in Treatment of Benign Prostatic Hypertrophy*, Urology, vol. VI, No. 5, Nov. 1975, pp. 580-587.

Tisell et al., *Androgenic Properties and Adrenal Depressant Activity of Megestrol Acetate Observed in Castrated Male Rats*, Acta Endocrinologica, vol. 78, 1975, pp. 316-324.

Burke et al., *Megestrol Acetate for Estrus Postponement in the Bitch*, JAVMA, vol. 167, No. 4, pp. 285-287.

Wait, *Megestrol Acetate in the Management of Advanced Endometrial Carcinoma*, Obstetrics and Gynecology, vol. 41, No. 1, Jan. 1973, pp. 129-136.

Balin et al., *Low Dosage Megestrol Acetate Application as Contraceptive*, The Journal of Reproductive Medicine, vol. V, No. 1, Jul. 1979, pp. 74-81.

Cooper et al., *The Metabolism of Megestrol Acetate (17 ∀-Acetoxy-6-Methylpregna-4,6-Diene-3,20-Dione) in Women*, Steroids, vol. 11, No. 2, Feb. 1968, pp. 133-149.

International Search Report corresponding to PCT/US 02/15690 mailed on May 12, 2002.

O'Connor, Vivenne M. "Managing Menopause: Part 2: what are the choices in treatment?" *MedicineToday* pp. 30-40 Feb. 2001.

David et al., *Anti-Ovulatory and Other Biological Properties of Megestrol Acetate 17 ∀-Acetoxy-6 Methyl Pregna 4:6-Diene-3:20-Dione (B.D.H. 1298)*. J. Reprod. Fertil., vol. 5, 1963, pp. 331-346.

Office Action corresponding to Canadian Patent Application No. 2,446,849 dated Apr. 20, 2011.

Davis et al. "Androgen Replacement in Women", *Contemporary Endocrinology Hormone Replacement Therapy* Chapter 22:401-417 (1999).

Examination Report corresponding to European Application No. 02736946.1 dated Jun. 29, 2011.

Wentz "Progestin Therapy in Endometrial Hyperplasia", *Gynecologic Oncology* 2:362-367 (1974).

* cited by examiner

TREATMENT OF CONDITIONS RELATING TO HORMONE DEFICIENCIES BY ADMINISTRATION OF PROGESTINS

CROSS REFERENCE TO RELATED APPLICATIONS

The present application is continuation application of U.S. patent application Ser. No. 12/912,352 filed Aug. 15, 2008, now U.S. Pat. No. 7,683,047, which is a divisional application of and claims priority from U.S. patent application Ser. No. 10/678,828 filed Oct. 3, 2003, now U.S. Pat. No. 7,427,609. U.S. patent application Ser. No. 10/678,828 is a continuation application of and claims priority from U.S. patent application Ser. No.10/147,366 filed May 16, 2002, now abandoned, which claims priority from U.S. Patent Application No. 60/291,488 May 16, 2001. The disclosure of each U.S. patent application cited above is hereby incorporated by reference in its entirety.

FIELD OF THE INVENTION

The invention relates to a method for administering agents that treat symptoms and conditions related to hormonal deficiencies. In particular, the present invention relates to the administration of estrogens and progestins such that an acceptable bleeding pattern is achieved and maintained during the treatment period.

BACKGROUND OF THE INVENTION

Natural menopause typically occurs in women during middle age and is often described as an ovarian shutdown. Menopause is associated with a profound decrease in circulating levels of estrogens. Currently, there are a large variety of disorders and conditions that are attributed to the reduction of estrogen levels. These disorders and conditions include hot flashes, dryness and atrophy of the vagina, parathesia, dyspareunia, osteoporosis, female sexual dysfunction, and an increase in cardiovascular disease. In an effort to reduce these disorders and conditions, estrogens are administered to women in a so-called "estrogen replacement therapy". Estrogen replacement therapy continues to be the primary treatment of such disorders and conditions associated with menopause.

Women, particularly perimenopausal, menopausal and postmenopausal women, often experience a wide variety of conditions and disorders attributable to estrogen deprivation. Estrogen deprivation is most often the result of loss of ovarian function. Providing dosages of estrogen is effective for the control or prevention of such conditions, particularly in controlling or preventing hot flashes and vaginal atrophy, along with retarding or preventing osteoporosis. Estrogen is typically administered alone or in combination with progestin.

As disclosed in U.S. Pat. No: Re. 36,247 to Plunkett et al., estrogen alone, given in small doses, on a continuous basis, is partially effective in patients for the control of the above symptoms and problems associated therewith. However, women who continuously take low-dose estrogen may risk developing endometrial hyperplasia, possibly leading to uterine carcinoma.

Approximately ten percent of women who are administered cyclic estrogen replacement therapy experience withdrawal bleeding between the cycles of the estrogens prescribed. To help reduce the development of endometrial hyperplasia, a progestin agent is often administered during the last 7-10 days of each estrogen cycle (of 28 to 30 days). When the progestin agent is administered cyclically, for example, during the last seven to ten days of the cycle, withdrawal bleeding regularly occurs. See, Whitehead, Am. J. Obs/Gyn., 142, 6, 791-795 (1982). When the progestin agent is administered continuously, random bleeding occurs, which is referred to as "breakthrough bleeding".

There are numerous other estrogen/progestin regimens that have been suggested for treatment of menopausal symptoms. For example, U.S. Pat. No. 4,425,339, issued to Pitchford, discloses a method for treating menopausal symptoms including a four phase sequence of estrogen and progestogen administration. U.S. Pat. No. 5,043,331, issued to Hirvonen et al., discloses a lengthy three step process of estrogen and progestogens. U.S. Pat. No. 5,827,843, issued to Koninckx, discloses a preparation for substitution therapy and oral contraception wherein at least one progestogen and at least one estrogen is administered. U.S. Pat. No. 5,891,867, issued to Lanquetin et al., relates to a method of treating estrogen deficiencies in menopausal women using three different sequences of an estrogen followed by an estrogen progestogen combination and a placebo over the duration of a month. U.S. Pat. No. 5,108,995, issued to Casper et al., discloses a hormone preparation and method wherein the doses are arranged in alternating estrogen dominant phases and progestin dominant phases and each phase consists of from one to four consecutive daily unit doses. Finally, U.S. Pat. No. 5.208,225, issued to Boissonneault et al., discloses compositions that contain fixed combinations of a synthetic estrogen and a synthetic progestogenic agent. However, despite the administration of the above therapies there is room for improvement to treat vasomotor symptoms. Thus, it may be desirable to relieve vasomotor symptoms through alternative methods of estrogen therapy using a progestin agent.

SUMMARY OF THE INVENTION

The present invention relates to a method for treating conditions related to hormone deficiencies comprising continuously administering at least one estrogen and at least one progestin wherein the amount of estrogen is substantially constant and the amount of progestin is decreased in at least one step from an amount sufficient to establish a nonproliferative endometrium to an amount that maintains the nonproliferative endometrium.

The present invention particularly relates to methods for treating physical conditions related to vasomotor symptoms, brought about by the onset of menopause. The method of the invention provides a method of treating a subject by administering a therapeutically effective amount of two or more dosage levels of progestin wherein the dosage levels of progestin decrease stepwise during the treatment period. The conditions treated include vasomotor symptoms, atrophic vaginitis, and osteoporosis, among others.

DETAILED DESCRIPTION OF THE INVENTION

The invention will now be described with reference to the embodiments set forth herein. These embodiments are intended to illustrate the invention and are not meant to limit the scope of the invention.

In one aspect, the invention relates to a method of administering a pharmaceutical composition. The pharmaceutical composition comprises a therapeutically effective amount of a progestin agent and a pharmaceutically acceptable carrier. Additionally, the composition may contain an estrogenic compound. The composition also may contain an androgenic compound.

A "therapeutically effective" amount as used herein is an amount of an estrogenic compound that is sufficient to ameliorate symptoms exhibited by a subject. The therapeutically effective amount will vary with the age and physical condition of the patient, the severity of the condition of the patient being treated, the duration of the treatment, the nature of any concurrent treatment, the pharmaceutically acceptable carrier used and like factors within the knowledge and expertise of those skilled in the art. Pharmaceutically acceptable carriers are preferably solid dosage forms such as tablets or capsules. Liquid preparations for oral administration also may be used and may be prepared in the form of syrups or suspensions, e.g., solutions containing an active ingredient, sugar, and a mixture of ethanol, water, glycerol, and propylene glycol. If desired, such liquid preparations may include one or more of following: coloring agents, flavoring agents, and saccharin. Additionally, thickening agents such as carboxymethylcellulose also may be used as well as other acceptable carriers, the selection of which are known in the art.

A progestin agent may be used in combination with the estrogenic compound. Examples of progestin agents are set forth in U.S. Pat. No. Re. 36,247 to Plunkett et al. Examples include, but are not limited to, di-norgestrel, norethindrone (norethisterone), norethindrone (norethisterone) acetate, ethynodiol diacetate, dydrogesterone, medroxyprogesterone acetate, norethynodrel, allylestrenol, lynoestrenol, quingestanol acetate, medrogestone, norgestrienone, dimethisterone, ethisterone, cyproterone acetate, desogestrel, levonorgestrel, hydroxyprogesterone caproate, 19-nortestosterone, chlormadinone acetate, megestrol acetate, norgestimate, norgestrel, trimegestone, gestodene, normegestrel acetate, progesterone, 5α-pregnan-3β, 20β-diol sulfate, 5α-pregnan-3β-ol-20-one, 16,5α-pregnen-3β-ol-20-one and 4-pregnen-20β-ol-3-one-20-sulfate.

As stated above, an estrogenic compound may be combined with the progestin agent. Estrogen levels are related to the general physiological health of menopausal, perimenopausal, and postmenopausal women. They exert positive central nervous system (CNS) effects on hot flashes, and improve nerve transmission, which is believed to delay various types of dementia. They have positive cardiovascular effects by improving lipid levels and promoting vasodilation and relaxation. They also contribute to health of the vagina, provide local vasodilation effects and stimulate mucous production. Suitable estrogenic compounds include estrone, 17α-estradiol, 17β-estradiol, equilin, 17α-dihydroequilin, 17β-dihydroequilin, equilenin, 17α-dihydroequilenin, 17β-dihydroequilenin, Δ8,9-dehydroestrone, 17α Δ8,9-dehydroestradiol, 17β Δ8,9-dehydroestradiol, 6-OH equilenin, 6-OH 17α-dihydroequilenin, ethinyl estradiol, estradiol valerate, 6-OH 17β-dihydroequilenin, and mixtures, conjugates and salts thereof, and the estrogen ketones and their corresponding 17α- and 17-β hydroxy derivatives.

The estrogenic compounds also may be present as conjugated estrogens. Approximately 1.0 mg of 17β-estradiol is equivalent to 0.625 mg of conjugated estrogens. The conjugates may be various conjugates understood by those skilled in the art, including, but not limited to, sulfate and glucuronide. The most preferred estrogen conjugates are estrogen sulfates. The estrogenic compounds also may be present as salts of estrogens conjugates. The salts may be various salts understood by those skilled in the art, including, but not limited to, sodium salts, calcium salts, magnesium salts, lithium salts, and piperazine salt. The most preferred salts are sodium salts. The estrogenic compounds can be derived from natural and synthetic sources. Preferably, the therapeutically effective amount of estrogenic compound is about 0.05 to about 3 mg, and preferably about 0.5 to about 2 mg based on oral dose equivalents of estradiol.

The amount of estrogen utilized preferably will remain substantially constant throughout the treatment period. In one aspect of the invention, the amount of estrogen will be an amount equivalent to from about 0.05 to about 5 mg conjugated estrogens. In a preferred aspect of the invention, the amount of estrogen will be an amount equivalent to from about 0.15 to about 1.25 mg conjugated estrogens for solid doses and 0.01 to 1 mg for topical and transdermal doses. In a more preferred aspect of the invention, the amount of estrogen will be at either an oral dosing strength of an equivalent of about 0.45 mg conjugated estrogens or an equivalent of about 0.625 mg conjugated estrogens.

The therapeutically effective dosage of any specific compound, the use of which is in the scope of present invention, will vary from compound to compound and patient to patient and condition to condition, and will depend upon factors such as the age, weight, and condition of the patient and the route of delivery. As a general proposition, a dosage from about 0.001 or 0.1 mg/kg to about 50, 100 or 500 mg/kg may have therapeutic efficacy, with all weights being calculated based upon the weight of the active compound, including the cases where a salt is employed.

Androgenic compounds may be combined with the progestin agents and estrogenic compounds. Suitable androgenic compounds include both aromatizing and non-aromatizing compounds. Acceptable compounds include, but are not limited to, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-17-benzoate, oxandrolone, oxymetholone, stanozolol, testosterone, testosterone decanoate, 4-dihydrotestosterone, 5α-dihydrotestosterone, testolactone, 17α-methyl-19-nortestosterone, xandrolone, oxymetholone, stanozolone, danazol, and pharmaceutically acceptable esters and salts thereof, as well as combinations of any of the foregoing. Preferably, the therapeutically effective amount of the androgenic compound is about 0.15 to about 10 mg. For women suffering from androgen deficiency the oral dosage equivalents of oxandrolone is about 0.5 to 5 mg of an androgenic compound per day. Additionally, preferably the therapeutically effective amount of the androgenic compound is equivalent to oral doses of about 0.15 to about 2.5 mg of methyl testosterone.

The estrogen formulations of the present invention may be, for example, in the faun of tablets; effervescent tablets; pills; powders; elixirs; suspensions; emulsions; solutions; syrups; soft and hard gelatin capsules; transdermal patches; topical gels, creams and the like; vaginal suppositories such as gels and creams and the like; sterile injectable solutions; and sterile packaged powders, sublingual tablets, buccal tablets and buccal adhesive systems.

In certain embodiments, the drug product is present in a solid pharmaceutical composition that may be suitable for oral administration. A solid composition of matter according to the present invention may be formed and may be mixed with and/or diluted by an excipient. The solid composition of matter also may be enclosed within a carrier, which may be, for example, in the form of a capsule, sachet, tablet, paper, or other container. When the excipient serves as a diluent, it may be a solid, semi-solid, or liquid material which acts as a vehicle, carrier, or medium for the composition of matter.

Various suitable excipients will be understood by those skilled in the art and may be found in the *National Formulary*, 19: 2404-2406 (2000), the disclosure of pages 2404 to 2406 being incorporated herein in their entirety. Examples of suitable excipients include, but are not limited to, starches, gum arabic, calcium silicate, microcrystalline cellulose, methacrylates, shellac, polyvinylpyrrolidone, cellulose, water, syrup, and methylcellulose. The drug product formulations additionally can include lubricating agents such as, for example, talc, magnesium stearate and mineral oil; wetting agents; emulsifying and suspending agents; preserving agents such as methyl- and propyl hydroxybenzoates; sweetening agents; or flavoring agents. Polyols, buffers, and inert fillers also may be used. Examples of polyols include, but are not limited to, mannitol, sorbitol, xylitol, sucrose, maltose, glucose, lactose, dextrose, and the like. Suitable buffers include, but are not limited to, phosphate, citrate, tartarate, succinate, and the like. Other inert fillers that may be used include those that are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the art.

To form tablets for oral administration, the composition of matter of the present invention may be made by a direct compression process. In this process, the active drug ingredients may be mixed with a solid, pulverant carrier such as, for example, lactose, saccharose, sorbitol, mannitol, starch, amylopectin, cellulose derivatives or gelatin, and mixtures thereof, as well as with an antifriction agent such as, for example, magnesium stearate, calcium stearate, and polyethylene glycol waxes. The mixture may then be pressed into tablets using a machine with the appropriate punches and dies to obtain the desired tablet size. The operating parameters of the machine may be selected by the skilled artisan. Alternatively, tablets for oral administration may be formed by a wet granulation process. Active drug ingredients may be mixed with excipients and/or diluents. The solid substances may be ground or sieved to a desired particle size. A binding agent may be added to the drug. The binding agent may be suspended and homogenized in a suitable solvent. The active ingredient and auxiliary agents also may be mixed with the binding agent solution. The resulting dry mixture is moistened with the solution uniformly. The moistening typically causes the particles to aggregate slightly, and the resulting mass is pressed through a stainless steel sieve having a desired size. The mixture is then dried in controlled drying units for the determined length of time necessary to achieve a desired particle size and consistency. The granules of the dried mixture are sieved to remove any powder. To this mixture, disintegrating, antifriction, and/or anti-adhesive agents may be added. Finally, the mixture is pressed into tablets using a machine with the appropriate punches and dies to obtain the desired tablet size. The operating parameters of the machine may be selected by the skilled artisan.

If coated tablets are desired, the above prepared core may be coated with a concentrated solution of sugar or cellulosic polymers, which may contain gum arabic, gelatin, talc, titanium dioxide, or with a lacquer dissolved in a volatile organic solvent or a mixture of solvents. To this coating various dyes may be added in order to distinguish among tablets with different active compounds or with different amounts of the active compound present. In a particular embodiment, the active ingredient may be present in a core surrounded by one or more layers including enteric coating layers.

Soft gelatin capsules may be prepared in which capsules contain a mixture of the active ingredient and vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, and/or gelatin.

In one preferred embodiment, the formulation is in the form of orally-administered tablets that contain the composition of matter of the present invention as set forth herein along with the following inactive ingredients: calcium phosphate tribasic, calcium sulfate, carnauba wax, cellulose, glyceryl monooleate, lactose, magnesium stearate, methylcellulose, pharmaceutical glaze, polyethylene glycol, stearic acid, sucrose, and titanium dioxide. Such ingredients may be present in amounts similar to those present in Premarin® (conjugated estrogens tablets, USP) made commercially available by Wyeth-Ayerst Laboratories of Philadelphia, Pa. Tablets employing the active ingredients of the invention may contain excipients similar to those contained in the 0.3 mg, 0.625 mg, and 1.25 mg tablets of Premarin® (conjugated estrogens tablets, USP).

Liquid preparations for oral administration may be prepared in the form of syrups or suspensions, e.g., solutions containing an active ingredient, sugar, and a mixture of ethanol, water, glycerol, and propylene glycol. If desired, such liquid preparations may comprise one or more of following: coloring agents, flavoring agents, and saccharin. Thickening agents such as carboxymethylcellulose also may be used.

In the event that the above pharmaceuticals are to be used for parenteral administration, such a formulation may comprise sterile aqueous injection solutions, non-aqueous injection solutions, or both, comprising the composition of matter of the present invention. When aqueous injection solutions are prepared, the composition of matter may be present as a water soluble pharmaceutically acceptable salt. Parenteral preparations may contain anti-oxidants, buffers, bacteriostats, and solutes which render the formulation isotonic with the blood of the intended recipient. Aqueous and non-aqueous sterile suspensions may comprise suspending agents and thickening agents. The formulations may be presented in unit-dose or multi-dose containers, for example sealed ampules and vials. Extemporaneous injection solutions and suspensions may be prepared from sterile powders, granules and tablets of the kind previously described.

In a preferred embodiment, the drug product of the present invention is in the form of an injectable solution containing a predetermined amount (e.g., 25 mg) of the composition of matter in a sterile lyophilized cake that also contains lactose, sodium citrate, and simethicone. The pH of a solution containing the above ingredients may be adjusted using a suitable buffer (e.g., sodium hydroxide or hydrochloric acid). Reconstitution may be carried out according to known methods, e.g., using a sterile diluent (5 mL) containing 2 percent by volume benzyl alcohol in sterile water. A preferred injectable solution is similar to Premarin® Intravenous made commercially available by Wyeth-Ayerst Laboratories.

The composition of matter also may be formulated such that it may be suitable for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol, monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

The drug product may be in the form of a vaginal cream containing the composition of matter as set forth herein present in a nonliquefying base. The nonliquefying base may contain various inactive ingredients such as, for example, cetyl esters wax, cetyl alcohol, white wax, glyceryl monostearate, propylene glycol monostearate, methyl stearate, benzyl alcohol, sodium lauryl sulfate, glycerin, propylene glycol and mineral oil. Such composition may be formulated similar to Premarin® Vaginal Cream made commercially available by Wyeth-Ayerst Laboratories.

Dosage units for vaginal or rectal administration may be prepared in the form of suppositories that may contain the composition of matter in a mixture with a neutral fat base, polyethylene glycol, or they may be prepared in the form of gelatin-rectal capsules that contain the active substance in a mixture with a vegetable oil or paraffin oil.

In the treatment of conditions relating to hormone deficiencies such as in the treatment of menopausal symptoms or in hormone replacement therapy, one issue of relative importance includes the absence of spotting or breakthrough bleeding when a subject takes a progestin agent. The methods and preparations of the present invention may be useful in alleviating menopausal symptoms and in providing long-term benefits and protection for women with decreasing hormone levels. The present invention also may provide a long-term solution to spotting and bleeding problems manifested with other treatment regimens. The present invention includes methods that may solve problems with spotting and bleeding during an estrogen treatment period. A reduction in bleeding may occur by initiating therapy with a progestin dose higher than that required to maintain therapy. The methods of the present invention also may maintain a substantially atrophic endometrium. Although traditional therapies utilized low progestin dosages, the present invention discloses that by providing a higher dose of progestin during a first portion of the treatment period and then lowering the dose of progestin to a maintenance dose, a reduction in spotting and bleeding problems may occur. The higher dose initiation period may extend from about seven days to about two months and may be stepped down gradually to a maintenance dose, or can be stepped down in one, two or more stages, as is known in the art.

In one embodiment, the first phase or initiation step of the treatment period may assist in controlling or inhibiting the estrogen induced proliferation of the endometrium of the uterus during the initiation of hormone replacement therapy and facilitate development of an atrophic endometrium. Once the controlling or inhibiting has been achieved, the step down in dosage of progestin may help maintain a substantially atrophic endometrium. Additionally, an initial dose of up to at least 400 mg of a progestin agent, based on dose equivalents to orally administered megestrol acetate may be administered to achieve a substantially atrophic endometrium.

The methods, preparations and pharmaceutical products of the present invention may provide for at least two or more dosage strengths over the course of the treatment period such that the dosages, when administered as provided herein, may result in an acceptable bleeding pattern. The initial dosing of the progestin may be relatively high to assist in inducing or establishing a nonproliferative endometrium. Typically, this effect may be evidenced by an absence of substantive mitotic activity. The dosing may be used to enhance the formation of nonproliferative endometrium and results in a reduction of random bleeding during the remainder of the treatment period. This dosage strength typically is administered for about 7 to about 120 days. This time period may be less than 7 days depending on the dosage. Administration of a high dosage may allow for a shorter initial period. The dosage amount of progestin is then either gradually reduced in a series of steps or is reduced in one step to a maintenance amount that is less than the initiation amount. The maintenance dose preferably is at least about 25% less than the initial dose and, most preferably, the maintenance amount is about half of the initiation dosage. More preferably the second dose is at least a 50% reduction than the initial dose of progestins. Subsequent doses may be greater than 50%, i.e., administering 400 mg in the first dose and dropping the dose all the way to 2 mg. At this point in the treatment period, the dosage amount is such that the nonproliferative or atrophic endometrium is maintained or continued. This dosage amount of progestin inhibits or decreases the potential for breakthrough bleeding and spotting, typical problems in traditional therapies. This dosage strength is typically administered for about two to four weeks for short-term therapies or may be administered indefinitely for longer therapies. The treatment period ends upon cessation of administration of the estrogen and progestin therapy.

In one embodiment of the invention, the amount of progestin is provided in an initiation step of the treatment period in an amount exhibiting progestin activity equivalent to above 10.0 mg of megestrol acetate and is provided in a maintenance step during the treatment period in an amount exhibiting progestin activity equivalent to below about 10.0 mg of megestrol acetate. Preferably, the amount of progestin activity is reduced by at least 25%; most preferably the amount of progestin is 50% the amount in the maintenance step as the amount in the initiation step. In another aspect of the invention, the amount of progestin preferably is decreased in a series of steps to the maintenance step wherein the progestin activity is about half the amount administered in the initiation dosage.

In another embodiment of the invention, the progestin is provided in an initiation step of the treatment in an amount exhibiting progestin activity equivalent to an oral dose of about 1 mg to about 40 mg of metzestrol acetate and is provided in a maintenance step during the treatment period in an amount exhibiting progestin activity equivalent to an oral dose of about 0.5 to about 10 mg of megestrol acetate; provided, however, that the amount of progestin activity is reduced in the maintenance step by at least 25%; most preferably the amount of progestin is 50% the amount in the maintenance step as the amount in the initiation step. A third step is most preferably reduced by an additional 50% from the second step.

In another embodiment of the present invention, the amount of progestin when the amount of estrogen is about 0.625 mg, may be either about 6 mg or about 12 mg in the initiation step and about 3 mg or about 6 mg, respectively, in the remaining or maintenance step of the treatment period. When the amount of estrogen is about 0.45 mg, the amount of progestin is preferably 5 mg or 10 mg, respectively, in the initiation step of the treatment period and approximately 2.5 mg or 5 mg in the remaining step or maintenance step of the treatment period. All amounts of progestin are in terms of biological equivalence to oral doses of megestrol acetate and all amounts of estrogen are in terms of biological equivalence to oral doses of conjugated estrogens. One skilled in the art will be able to compare the dose equivalency tables should they choose a progestin outside of megestrol acetate.

Thus, the methods used in the present invention may include reducing the amount of a progestin given to a subject by starting out administering a high dose of a progestin agent to a subject and then gradually lowering the dose once therapy has been effectively established. One skilled in the art will be able to use a number of permutations in that the dosage of the progestin agent may be lowered. Additionally, once therapy has been effectively established it may be possible to continue the step-down therapy as disclosed above by decreasing the amount of progestin agent in a third or fourth dose. One skilled in the art will be able to choose additional regimens based upon this information.

The first dose may be administered daily, continuously and uninterruptedly for an effective time period until such time that therapy has been effectively established, preferably one week to two months, more preferably two to six weeks.

The initiation dosage amount of progestin may be sufficient to enhance formulation of or may help establish a non-proliferative or atrophic endometrium. The treatment may further substantially induce bleeding and then obviate or reduce random bleeding. The maintenance dosage amount is sufficient and effective for continuing or maintaining the non-proliferative endometrium established by the initiation dosage of progestin. The maintenance dosage amount further inhibits and decreases breakthrough bleeding and spotting observed in traditional therapies.

The methods may be used for a number of treatments such as, but not limited to, vasomotor symptoms; atrophic vaginitis; osteoporosis; hypoestrogenism due to hypogonadism, castration, or other primary ovarian failure, among others. The administration of estrogen and progestin according to the present invention may be continuous for a short-term, for example, to treat vasomotor symptoms, or may be continuous for a long-term, for example for osteoporosis. One example of long-term use would be from the onset of menopause until death.

The pharmaceutical product of the invention may be provided in a variety of forms, such that the sequential dosage units may be easily accessible by a subject. For example, the pharmaceutical product may be provided as a pharmaceutical package containing the sequential dosages in an arrangement suitable for daily administration of the appropriate dosages of estrogen and progestin. The number of dosages in each package may depend on the therapy and whether it is a long-term therapy for hormone deficiencies, or a short-term therapy. Typically, the pharmaceutical product may include a kit or package with daily dosages arranged for proper sequential administration. The sequence or arrangement of the dosage units will correspond to the stages of daily administration.

The present invention is primarily concerned with the treatment of human subjects, but the invention also may be carried out on animal subjects, particularly mammalian subjects such as mice, rats, dogs, cats, livestock and horses for veterinary purposes, and for drug screening and drug development purposes.

The present invention is explained in greater detail in the Examples, which follow. These examples are intended as illustrative of the invention and are not to be taken as limiting thereof.

EXAMPLES

The present invention includes methods for treating conditions associated with hormone deficiencies and comprises administering daily, continuously and uninterruptedly, during a treatment period, at least one estrogen in a substantially constant amount exhibiting oral estrogen activity equivalent to from about 0.05 to about 3 mg of conjugated estrogens; continuously and uninterruptedly administering at least one progestin in an initiation step in an amount exhibiting progestin activity equivalent to about 12.0 mg of megestrol acetate; and continuously administering at least one progestin in a maintenance step in an amount exhibiting progestin activity equivalent to about 6.0 mg of megestrol acetate. In this embodiment the estrogenic compound was administered at approximately 0.625 mg continuously and uninterruptedly daily.

The subjects' initiation step of the treatment period preferably is from about 7 days to about 60 days. The maintenance step of the treatment period may be from about 60 days to about 120 days for short-term treatment of conditions related to hormone deficiency. In the alternative, the maintenance step of the treatment period may be continued indefinitely for treatment of long-term conditions related to hormone deficiencies.

A randomized study was performed comparing subjects administered the 50% step-down progestin program as compared to those who were administered a continuous and uninterrupted dose of a progestin agent. The results of the study as exhibited in table 1 below help demonstrate the effectiveness of the step down method.

TABLE 1

| Step Down Method | Patient 1 | Patient 2 | Patient 3 | Patient 4 | Patient 5 | Patient 6 | Patient 7 |
|---|---|---|---|---|---|---|---|
| Bleeding Score | 0 | 0 | 0 | 0 | 0 | 0 | 16 |
| Continuous Method | Patient 8 | Patient 9 | Patient 10 | Patient 11 | Patient 12 | Patient 13 | Patient 14 | Patient 15 |
| Bleeding Score | 6 | 31 | 0 | 0 | 0 | 0 | 0 | 0 |

Table 1 shows a total of fifteen subjects who have been subjected to a randomized study. A first group of female subjects were administered the step-down method wherein the subjects were given 0.625 mg of conjugated estrogens in combination with 12 mg of megestrol acetate for the first two weeks and then 0.625 mg of conjugated estrogens in combination with 6 mg of megestrol acetate for the next ten weeks. The second group of subjects, as represented by the continuous method above, were given 0.625 mg of conjugated estrogens in combination with 6 mg of megestrol acetate for twelve weeks. A bleeding score was determined according to the following parameters: 0=no bleeding; 1=1 day of spotting; 2=1 day of slight bleeding; 3=1 day of moderate bleeding; and 4=1 day of heavy bleeding. Thus, the total bleeding score for subjects undergoing the step-down method was 16, and subjects undergoing the continuous method exhibited a bleeding score of 37. This score demonstrates a 57% decrease in bleeding for a subject undergoing the step-down method as compared to a continuous method.

Another randomized study using a three part step-down method also may assist in a reduction in the bleeding score. This study includes subjects undergoing a continuous treatment method wherein the subjects are administered the same level of a progestin agent continuously as compared to subjects undergoing the step-down method. Alternatively, under the step-down method, a subject may be administered an equivalent of 16 mg of a progestin agent, based on equivalent oral dosages to megestrol acetate for two weeks, then have 8 mg of a progestin agent administered for two weeks, and then have 4 mg of a progestin agent administered for ten weeks. Alternatively, the step-down method may include the administration of 8 mg of a progestin agent for two weeks, then 4 mg of a progestin agent for two weeks, and then 2 mg of a progestin agent for at least eight weeks. All doses are based on equivalent oral dosages to megestrol acetate. These step-down methods indicate the ability to decrease bleeding in a subject undergoing estrogen therapy.

In the specification, there has been disclosed typical preferred embodiments of the invention and, although specific terms are employed, they are used in a generic and descriptive sense only and not for purposes of limitation of the scope of the invention being set forth in the following claims.

What is claimed is:

1. A method of treating atrophic vaginitis in a subject, said method comprising:
   administering continuously and uninterruptedly for a first predetermined time period a first dose of a progestin agent to said subject; and
   administering continuously and uninterruptedly for a second predetermined time period a second dose of a progestin agent to said subject.

2. The method according to claim 1, wherein said progestin agent is selected from the group consisting of dl-norgestrel, norethindrone (norethisterone), norethindrone (norethisterone) acetate, ethynodiol diacetate, dydrogesterone, medroxyprogesterone acetate, norethynodrel, allylestrenol, lynoestrenol, quingestranol acetate, medrogestone, norgestrienone, dimethisterone, ethisterone, cyproterone acetate, desogestrel, levonorgestrel, hydroxyprogesterone caproate, 19-nortestosterone, chlormadinone acetate, megestrol acetate, norgestimate, norgestrel, trimegestone, gestodene, normegestrel acetate, progesterone, $5\alpha$-pregnan-$3\beta,20\beta$-diol sulfate, $5\alpha$-pregnan-$3\beta$-ol-20-one, $16,5\alpha$-pregnen-$3\beta$-ol-20-one and 4-pregnen-$20\beta$-ol-3-one-20-sulfate.

3. The method according to claim 1, wherein said first dose comprises an equivalent of 0.5 to 40 mg of a progestin agent, based on equivalent oral doses to megestrol acetate.

4. The method according to claim 1, wherein said first dose comprises an equivalent of 2 to 20 mg of a progestin agent, based on equivalent oral doses to megestrol acetate.

5. The method according to claim 1, wherein said second dose comprises an equivalent of 0.025 to 10 mg of a progestin agent, based on based on equivalent oral doses to megestrol acetate.

6. The method according to claim 1, further comprising administering an estrogenic compound in a daily dose.

7. The method according to claim 1, further comprising administering an androgen compound in a daily dose.

8. The method according to claim 1, wherein said first predetermined time period for said first dose of a progestin agent is at least two weeks before the administration of said second dose of a progestin agent.

9. The method according to claim 1, wherein said first predetermined time period for said first dose of a progestin agent is between two to twelve weeks before the administration of said second dose of a progestin agent.

* * * * *

UNITED STATES PATENT AND TRADEMARK OFFICE
CERTIFICATE OF CORRECTION

PATENT NO. : 8,076,319 B2
APPLICATION NO. : 12/700078
DATED : December 13, 2011
INVENTOR(S) : Leonard Page 1 of 1

It is certified that error appears in the above-identified patent and that said Letters Patent is hereby corrected as shown below:

On the Title Page:
Item (56) References, Other Publications, Page 2, Left Column, Line 1
  Please correct "Von Rocnn" to read -- Von Roenn --
Other Publications: Please add
  -- Medline Abstract No. 1998029329, Rickels et al., Journal of Clinical Psychiatry, (1997) 58 Suppl. 11,4-10 --

In the Patent:
Column 2, Line 27: Please correct "5.208,225" to read -- 5,208,225 --

Column 3, Lines 48-49:
  Please correct "Δ8,9-dehydroestrone, 17α Δ8,9-dehydroestradiol, 17β 8,9-dehydroestradiol"
  to read -- $\Delta^{8,9}$-dehydroestrone, 17α $\Delta^{8,9}$-dehydroestradiol, 17β $\Delta^{8,9}$-dehydroestradiol --

Column 6, Lines 21-22: Please correct by joining lines to make one paragraph
  to read: -- those present in Premarin® (conjugated estrogens --

Columns 9 and 10, Table 1: Please correct the alignment of the contents of Table 1 so that it reads as follows:

| Step Down Method | Patient 1 | Patient 2 | Patient 3 | Patient 4 | Patient 5 | Patient 6 | Patient 7 | |
|---|---|---|---|---|---|---|---|---|
| Bleeding Score | 0 | 0 | 0 | 0 | 0 | 0 | 16 | |
| Continuous Method | Patient 8 | Patient 9 | Patient 10 | Patient 11 | Patient 12 | Patient 13 | Patient 14 | Patient 15 |
| Bleeding Score | 6 | 31 | 0 | 0 | 0 | 0 | 0 | 0 |

Signed and Sealed this
Twenty-eighth Day of August, 2012

David J. Kappos
*Director of the United States Patent and Trademark Office*